_United States Patent_ [19]

Suzuki et al.

[11] Patent Number: 5,147,801
[45] Date of Patent: Sep. 15, 1992

[54] CULTURE MEDIUM DEVICE FOR BACTERIA

[75] Inventors: Akira Suzuki; Yuji Sakamoto; Yuko Masuda, all of Tokyo, Japan

[73] Assignee: Kirin Beer Kabushiki Kaisha, Tokyo, Japan

[21] Appl. No.: 452,767

[22] Filed: Dec. 19, 1989

[30] Foreign Application Priority Data

Dec. 21, 1988 [JP] Japan .................................. 63-322432

[51] Int. Cl.$^5$ ..................... C12M 1/16; B32B 23/08; C12Q 1/24
[52] U.S. Cl. ..................................... 435/299; 428/513; 428/537.5; 428/34.3; 435/30; 435/801; 435/805
[58] Field of Search .................. 428/537.5, 513, 34.3; 435/39, 30, 299, 805, 801

[56] References Cited

U.S. PATENT DOCUMENTS 4,476,226 10/1984 Hansen et al. ...................... 435/299
4,587,213 5/1986 Malecki ................................. 435/39

FOREIGN PATENT DOCUMENTS 739939 10/1943 Fed. Rep. of Germany ... 428/537.5
1032900 7/1953 France .............................. 428/537.5
1306147 9/1962 France .............................. 428/537.5

Primary Examiner—P. C. Sluby
Attorney, Agent, or Firm—Ladas & Parry

[57] ABSTRACT

A culture medium device in the form of a sheet comprises a base sheet member composed of an upper sheet having a hydrophilic property such as filter paper, a lower sheet having a water repellent property covering a lower surface of the upper hydrophilic sheet and a sheet member having a water repellent property preferably in the form of a film having a character suitable for bacteria to be treated. A gel agent or gelatinizer containing bacteria culturing nutrient is dispersed on an upper surface of the upper hydrophilic sheet of the base sheet member and the gel agent or gelatinizer is absorbed in the upper hydrophilic sheet and then solidified. The upper water repellent sheet member is applied so as to cover the upper surface of the upper hydrophilic sheet of the base sheet member.

6 Claims, 1 Drawing Sheet

CULTURE MEDIUM DEVICE FOR BACTERIA

BACKGROUND OF THE INVENTION

The present invention relates to a device for culturing microorganisms, and more particularly, to a culture medium in the form of a sheet for culturing adhesive bacteria and dropping bacteria, and a method of preparing the culture medium device.

A known sheet-form culture medium generally comprises laminated upper and lower sheet members. The upper sheet is peeled off at a time just before the usage thereof to permit aseptic water such as distilled water to be dropped onto the upper surface of the lower sheet to wet the same. A material or substance is thereafter inoculated to the central portion of the upper surface of the lower sheet by means of a pipette and the upper sheet is then covered over the lower sheet. A spreader made of a plastic material is placed on the upper surface of the upper sheet member at a portion corresponding to the location of the inoculated material on the lower sheet. A light pressure is then applied to the spreader to uniformly spread the inoculated material over substantially the entire upper surface of the lower sheet, whereby the material may be cultured.

In the preparation of the sheet-form culture medium in accordance with a conventional method described above, it is necessary to peel off the upper sheet and drop the aseptic water on the upper surface of the lower sheet before the usage of the culture medium; that is, the aseptic water must be transferred to a portion at which the aseptic water is actually used. In addition, contamination of the environment of the upper surface of the sheet, when the aseptic water is dropped on the upper surface of the lower sheet, has to be considered, since the sterilization of instruments or the like is required for every such application. These inconveniences require users to pay close attention to the treatment and operation of the culture medium preparation, therefore making it troublesome and time consuming.

SUMMARY OF THE INVENTION

An object of the present invention is to substantially eliminate defects or drawbacks encountered in the prior art described above and to provide a culture medium device, in the form of a sheet and a method of preparing the same, which is capable of being easily transferred and usable without requiring sterilization.

This and other objects can be achieved in one aspect according to the present invention by providing a culture medium device in the form of a sheet comprising a base sheet member composed of an upper sheet having a hydrophilic property and a lower sheet having a water repellent property and covering a lower surface of the upper hydrophilic sheet in which a gel agent or gelatinizer containing a bacteria culturing nutrient has been dispersed and then solidified, and a sheet member having a water repellent property for covering the upper hydrophilic sheet of the base sheet member.

In a preferred embodiment, the upper water repellent sheet member is formed of a film member selected in accordance with the bacteria to be treated. The hydrophilic sheet of the base sheet member is formed of a filter paper.

In another aspect according to the present invention, there is provided a method of preparing a culture medium device in the form of a sheet comprising the steps of preparing a base sheet member composed of an upper sheet having a hydrophilic property and a lower sheet having a water repellent property covering a lower surface of the upper hydrophilic sheet and preparing a sheet member having a water repellent property to cover the upper hydrophilic sheet of the base sheet member, preparing a gel agent or gelatinizer containing bacteria culturing nutrient, dispersing and solidifying the gel agent or gelatinizer on an upper surface of the upper hydrophilic sheet of the base sheet member, and applying the upper water repellent sheet member so as to cover the upper surface of the upper hydrophilic sheet of the base sheet member.

According to the present invention, the culture medium is prepared by dispersing the gel agent or gelatinizer containing the bacteria culturing nutrient on an upper surface of the hydrophilic sheet having a lower surface covered by the water repellent sheet whereby it is partially absorbed by the upper hydrophilic sheet, and solidifying the dispersed gel agent or gelatinizer on the upper hydrophilic sheet. The upper surface of the hydrophilic sheet thus prepared is then covered with the water repellent sheet member. Accordingly, the culture medium can be maintained without being dried. The inoculation can be performed immediately after peeling of the upper water repellent sheet member.

DESCRIPTION OF THE PREFERRED EMBODIMENTS

For a better understanding of the present invention, a conventional sheet-shaped culture medium will be described hereunder with reference to FIGS. 3 and 4 in the preparation thereof.

Figure 3:
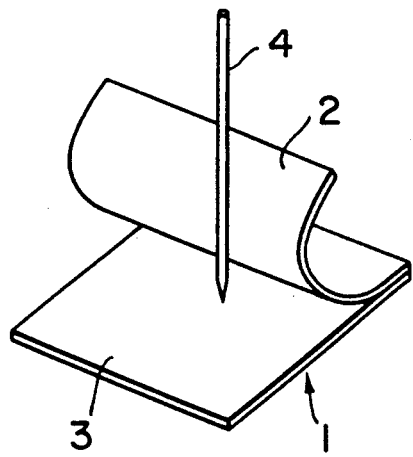
FIG. 3 is a view, according to a prior art, showing a state similar to that of FIG. 1.
Figure 4:
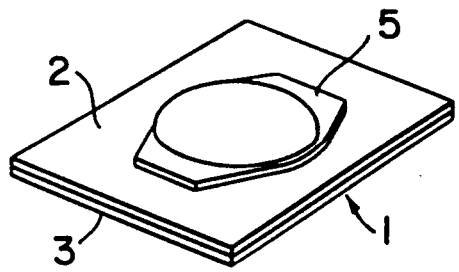
FIG. 4 is a perspective view of a conventional culture medium plate on which a spreader is placed.

Referring to FIG. 3, a culture medium sheet 1 generally comprises an upper sheet member 2 and a lower sheet member 3 which are laminated to each other. The upper sheet 2 is peeled off at a time just before the usage thereof to drop aseptic water such as distilled water on the upper surface of the lower sheet 3 to wet the same. When bacteria are made to adhere by, for example, pressing an upper surface of a lower sheet 3 against a sample or when a material has been inoculated by a pipette 4, the upper sheet 2 is then covered over the lower sheet 3. After the covering of the upper sheet 2, as shown in FIG. 5, a spreader 5 made of a plastic material is placed on the upper surface of the upper sheet 2 at a portion corresponding to the location of the inoculated material on the lower sheet 3. A light pressure is then applied to the spreader 5 to uniformly spread the material over substantially the entire upper surface of the lower sheet 3, whereby the material may be cultured.

However, the preparation of the culture medium sheet on the basis of the conventional method involves the inconveniences or problems described hereinbefore.

Preferred embodiments according to the present invention conceived by taking the above problems of the prior art into consideration will be described hereunder with reference to FIGS. 1 to 3, in which like reference numerals are added to elements or members corresponding to those shown in FIGS. 3 and 4.

Figure 1:
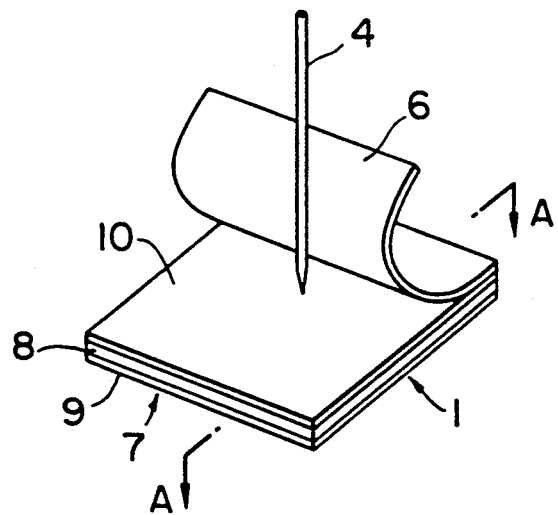
FIG. 1 is a perspective view of one embodiment of a culture medium device according to the present invention showing a state in which a material has just been inoculated by means of a pipette.
Figure 2:
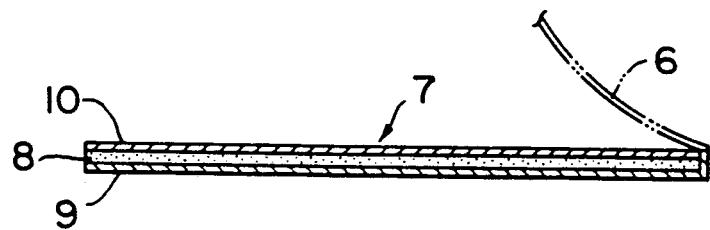
FIG. 2 is a sectional view taken along the line A—A shown in FIG. 1.

FIG. 1 shows a culture medium device in the form of a sheet according to the present invention having a square configuration, for example, having a side length of 50 mm and a thin thickness of 2 mm. The culture medium device 1 comprises an upper sheet 6 having a water repellent property and a lower base sheet 7. The upper water repellent sheet 6 is made of a material selected in accordance with the bacteria or microorganism to be treated. For example, with bacteria having an aerobic property, the water repellent sheet 6 is prepared by an oxygen permeable film and with the bacteria of an anaerobic property, the sheet 6 is prepared by an impermeable film. The upper water repellent sheet 6 thus may be prepared of a material such as polyethylene or polypropylene having a thickness of about 20μ. The lower base sheet 7 is composed of an upper sheet-like filter paper 8 having a hydrophilic property and a lower water repellent sheet 9 made of a material such as polyethylene and having a thickness of about 20μ. The lower water repellent sheet 9 is adhered to the upper filter paper 8 for maintaining the wetness of the filter paper 8 and for reinforcing the same. The upper water repellent sheet 6 and the lower base sheet 7 are laminated and bonded at one of their ends to allow the upper water repellent sheet 6 to be opened or rolled up as shown in FIG. 1 with respect to the lower base sheet 7.

In order to prevent the invasion of bacteria or germs when the culture medium device 1 is not used, the culture medium device 1 may be sealed in a bag made of, for example, a plastic material, or the outer peripheries of the upper water repellent sheet 6 and the lower water repellent sheet 9 may be bonded (fused) to seal them by means of separate tapes. Any other means may be applied to seal the culture medium device 1 to prevent the invasion of germs.

When aerobic bacteria are treated, it may be desirable to locate an air space between a gelled surface and the upper water repellent sheet 6 to introduce air therein.

The final culture medium 10 for the culture medium device 1 will be completed by preparing a gel agent or gelatinizer formed of sodium alginate of 0.5 to 4.0%, containing a bacteria culturing nutrient in the gel agent or gelatinizer, and dispersing the thus prepared gel agent or gelatinizer onto the sterilized filter paper 8 in a sterilized state. A sterilized color former such as 2,3,5-Triphenyl-2H-tetrazolium chloride (TTC)) may be contained in the alginic acid. The surface of the filter paper 8 may be held in a sterilized state by absorbing sterilized calcium chloride of 10 to 500 mM and the gel agent or gelatinizer is solidified on the filter paper 8 to form layer 10 as shown in FIGS. 1 and 2. The bacteria culturing nutrient may contain casein hydrolyzate of 1.5%, soybean pepton of 0.5%, and potassium chloride of 0.5% for bacteria and, for Eumycetes, glucose of 2.0%, yeast extract of 0.2%, magnesium sulfate of 0.05%, casein hydrolyzate of 0.5%, and potassium dihydrogen phosphate of 0.1%.

The culture medium device 1 in the form of a sheet of the character described above, may be utilized in the following manner.

The upper water repellent sheet 6 is peeled off from the filter paper 8 of base sheet 7, and bacteria are inoculated on the filter paper 8 by pressing a test sample containing bacteria against the final culture medium 10 on filter paper 8 or by introducing dropping bacteria to the final culture medium 10 on filter paper 8. The water repellent sheet 6 is then covered over the filter paper 8 whereby the material may be cultured. In a case of a liquid material, a small amount of the material is dropped or inoculated by a pipette 4 on the filter paper.

As described above, the filter paper 8 of the base sheet 7 has been made into a sterilized and gel state before using the sheet-like culture medium device 1, so that it is not necessary to wet the filter paper with an aseptic water such as distilled water. The sterilized state of the filter paper 8 can be maintained without being dried because the upper water repellent sheet 6 and the lower water repellent sheet 9 of the base sheet 7 are made of polyethylene having a water repellant property, for example.

In a modification, the culture medium device 1 may be accommodated in a bag having air-impermeability with a mouth portion sealed by a heat sealing method, for example, to stably maintain the sterilized condition. The bag may be further exposed to γ-rays or ultra violet rays for the sterilization of the culture medium device. The device may be sterilized by the utilization of gas (for example Ethylene Oxide Gas) or by an autoclave treatment.

In the described embodiment, the filter paper is utilized as a hydrophilic sheet, but a plastic sheet material or ceramic sheet material may be utilized.

The culture medium device according to the present invention may be utilized for elapsed time capture of bacteria, such as dropping bacteria, for environmental measurement and as a stamp for culturing adhesion bacteria.

Some concrete examples will be described hereunder in comparison with conventional examples.

EXAMPLE 1

Sodium alginate (30 g) was dissolved in a distilled water (1000 ml) and a sterilization dry culture medium (Trypticase soy Broth; BBL Co. Ltd.: 30 g) was thereafter dissolved to prepare a solution. A qualitative filter paper No. 2 of TOYO ROSHI having a size of 4×5 cm and preliminarily lined by a Polyethylene terephthalate film was impregnated in the thus prepared solution. The qualitative filter paper was dipped into 2% calcium chloride solution after being taken out from the aforementioned solution and gelled material. The gelled material was then covered with the PET film and sterilized by the autoclave treatment at 121° C. for 20 minutes.

COMPARATIVE EXAMPLE 1

Aseptic water was applied by 1 ml to a Petrifilm SM of 3M firm in accordance with a manual of 3M firm and disposed as it is for 20 minutes.

Bacteria adhesion tests were carried out with respect to the Example 1 and the Comparative Example 1. The tests were carried out by coating the Escherichia coli of a predetermined amount on a sterilized glass plate and then opening a cover. A sheet-form culture medium and the Petrifilm SM were pressed against the glass plate for about 10 seconds. Thereafter, the culture medium was covered and cultured at 37° C. for 24 hr. and the numbers of the cultured colonies were counted. The counting results are shown in the following Table 1.

TABLE 1

| | n = 10 |
|---|---|
| | Number of Colonies |
| Example 1 | 33 |
| Comparative Example 1 | 31 |

EXAMPLE 2

A culture medium was prepared by substantially the same manner as described with respect to the Example 1, sealed in a plastic bag, and then sterilized by the irradiation of γ-rays.

COMPARATIVE EXAMPLE 2

Trypticase soy Broth (30 g) and Agar (20.0 g) were dissolved in distilled water (1000 ml) into a solution. The solution was sterilized at 121° C. for 20 minutes by autoclave treatment. The solution was thereafter shared into sterilization Petri dishes each having a diameter of 50 mm and then solidified therein.

Dropping bacteria tests were carried out with respect to the Example 2 and the Comparative Example 2 by removing the cover of the culture medium and the cover of the Petri dish to catch and collect the dropping bacteria in a room for 5 minutes. Thereafter, the covers were applied and the cultured colonies were counted and the counting results are obtained as shown in the following Table 2.

TABLE 2

| | n = 10 |
|---|---|
| | Number of Colonies |
| Example 2 | 13 |
| Comparative Example 2 | 15 |

As described hereinabove, according to the adhesion bacteria tests and the dropping bacteria tests, substantially identical numbers of the colonies were observed with respect to the examples and the comparative examples. However, as described with respect to Example 2, when the culture medium is preliminarily prepared, it is not necessary to prepare distilled water and add the same to the culture medium 20 minutes before each test, as is necessary when using the Petrifilm. Moreover, it is also not necessary to prepare and sterilize the culture medium for each test as described with respect to the comparative example.

What is claimed is:

1. A culture medium device for culturing bacteria, said device comprising
   a) hydrophilic sheet means having top and bottom surfaces;
   b) a final culture medium comprising a gel agent or gelatinizer, a culturing nutrient for said bacteria, and water; said final culture medium being dispersed atop and partially absorbed by said hydrophilic sheet means and solidified thereon without being dried such that the final culture medium and hydrophilic sheet means are wet;
   c) lower sheet means for covering the bottom surface of said hydrophilic sheet means and for reinforcing the same;
   d) upper sheet means for covering the top surface of the hydrophilic sheet means with the final culture medium dispersed thereon; said upper and lower sheet mans being water repellant to maintain the wetness of the hydrophilic sheet means and the final culture medium whereby the bacteria can be cultured in the final culture medium without the addition of water prior to culturing.

2. A culture medium device as claimed in claim 1, further comprising bag means for sealing the culture medium device to prevent the invasion of germs.

3. A culture medium device as claimed in claim 1, wherein said hydrophilic sheet means comprises filter paper.

4. A culture medium device as claimed in claim 1, wherein the lower sheet means is adhered to the bottom surface of the hydrophilic sheet means and forms with the hydrophilic sheet means and the final culture medium lower base sheet means, and wherein the upper sheet means and the lower base sheet means each have two ends and are bonded together at one of their respective ends.

5. A culture medium device according to claim 1, wherein said upper sheet means is made of an oxygen permeable film for use with aerobic bacteria.

6. A culture medium device according to claim 1, wherein said upper sheet means is made of an impermeable film for use with anaerobic bacteria.

* * * * *